United States Patent
Takeuchi et al.

(10) Patent No.: US 8,400,498 B2
(45) Date of Patent: *Mar. 19, 2013

(54) ENDOSCOPE APPARATUS

(75) Inventors: Shinji Takeuchi, Saitama (JP); Mitsuru Higuchi, Saitama (JP); Kazunori Abe, Saitama (JP)

(73) Assignee: FUJINON Corporation, Saitama-shi (JP)

( * ) Notice: Subject to any disclaimer, the term of this patent is extended or adjusted under 35 U.S.C. 154(b) by 1870 days.

This patent is subject to a terminal disclaimer.

(21) Appl. No.: 11/546,475

(22) Filed: Oct. 12, 2006

(65) Prior Publication Data

US 2007/0088192 A1    Apr. 19, 2007

(30) Foreign Application Priority Data

Oct. 14, 2005  (JP) .............................. P2005-300193

(51) Int. Cl.
  *A62B 1/04*  (2006.01)
(52) U.S. Cl. ................ 348/65; 348/45; 348/46; 348/72; 348/71
(58) Field of Classification Search .............. 348/65, 348/45, 46, 72, 71
See application file for complete search history.

(56) References Cited

U.S. PATENT DOCUMENTS

| 4,885,634 | A | * | 12/1989 | Yabe | ............................... | 348/71 |
| 5,206,817 | A | * | 4/1993 | McClure | .................. | 365/189.15 |
| 5,255,087 | A | * | 10/1993 | Nakamura et al. | .............. | 348/71 |
| 2004/0215060 | A1 | | 10/2004 | Ueno et al. | | |

FOREIGN PATENT DOCUMENTS

| EP | 1 698 272 A2 | 9/2006 |
| JP | 2003-93336 A | 4/2003 |

OTHER PUBLICATIONS

Miyake, Y., 2000, pp. 148-153, University Tokyo Press.

* cited by examiner

*Primary Examiner* — Lan-Dai T Truong
(74) *Attorney, Agent, or Firm* — Birch, Stewart, Kolasch & Birch, LLP

(57) ABSTRACT

An endoscope having a color space conversion circuit performs a matrix calculation according to RGB signals and matrix data respectively corresponding to signals in wavelength ranges is provided with a wavelength memory section having a default data memory area, which stores a default value representing a wavelength range selected by a wavelength selection section, and a changed-wavelength saving area that stores a wavelength range selected by the wavelength selection section after changed from the wavelength range represented by the default value. Subsequently, at least a part of the wavelength range stored in the changed-wavelength saving area is rewritten by a reset section into the default value stored in the default data memory area.

4 Claims, 5 Drawing Sheets

FIG. 6

| λ1 | λ2 | λ3 |
|---|---|---|
| 400 | 500 | 600 |
| ↓ | ↓ | ↓ |
| 405 | 510 | 620 |
| ↓ | ↓ | ↓ |
| 410 | 520 | 640 |
| ↓ | ↓ | ↓ |
| 415 | 530 | 660 |
| ↓ | ↓ | ↓ |

FIG. 7

(MONOCHROMATIC MODE, SINGLE WAVELENGTH SET)

| λ1 | λ2 | λ3 |
|---|---|---|
| 470 | 470 | 470 |
| ⋮ | | |
| 500 | 500 | 500 |
| ⋮ | | |
| 530 | 530 | 530 |

ENDOSCOPE APPARATUS

BACKGROUND OF THE INVENTION

1. Field of the Invention

The present invention relates to an endoscope and, more particularly, to the constitution of an apparatus for use in a medical field for forming and displaying a spectral image (or video image), which is represented by image information obtained in an optionally selected wavelength range.

2. Description of the Related Art

In recent years, among electronic endoscope apparatuses employing solid-state image pickup devices, an electronic endoscope adapted to perform spectroscopic imaging by combining narrow band bandpass filters according to spectral reflectance obtained at a digestive organ, such as gastric mucosa, that is, an electronic endoscope apparatus with a built-in narrow band bandpass filter (or NBI (narrow band imaging) filter) has received attention. This apparatus is provided with three narrow (wavelength) band bandpass filters, instead of frame sequential type RGB rotary filters. The apparatus sequentially outputs illuminating light rays through these narrow band bandpass filters. Then, the apparatus performs processing similar to that performed on R, G, and B (RGB) signals by simultaneously changing weights assigned to three signals obtained by these illuminating light rays. Consequently, the apparatus forms a spectral image. According to such a spectral image, a microstructure, which could not be obtained in a digestive organ such as a large or small bowel by a related apparatus, is extracted.

Meanwhile, it has been proposed to form a spectral image by performing computation according to an image signal, which is obtained by white light, in an endoscope apparatus of the synchronous system type configured to dispose minute mosaic color miters at a solid-state image pickup device as disclosed in JP-A-2003-93336 and Yoichi Miyake: *Analysis and Evaluation of Digital Color Images*, University of Tokyo Press, pp. 148 to 153 (2000), instead of the above endoscope apparatus of the frame sequential type using the narrow band bandpass filters. The proposed apparatus first obtains matrix data (representing a coefficient set) representing the relation between numerical data, into which an RGB color sensitivity characteristic is converted, and numerical data, into which a spectral characteristic of a specific narrow band bandpass filter is converted. Then, the proposed apparatus obtains spectral-image signals representing an estimated spectral image through narrow band bandpass filters by performing computation on the matrix data and RGB-signals. In the case of forming a spectral image by such computation, there is no need for preparing a plurality of filters respectively corresponding to a desired wavelength range. Also, the proposed apparatus eliminates the replacement of such filters. Thus, the size of the apparatus is prevented from being made to be large. Consequently, the cost of the apparatus can be reduced.

Incidentally, a wavelength range optimal in forming and displaying a clinically easily observable spectral image often varies with operators, such as a clinical doctor, of the apparatus. Thus, even in a case where a wavelength range considered to be optimal for a part of an object to be observed is preliminarily set in the apparatus, a clinical doctor may be unable to utilize the set wavelength range at the formation of a spectral image and to help selecting a wavelength range conforming to his feeling.

In such a case, the operator gradually changes the preliminarily set wavelength range. To perform such a changing operation, it is preferable to provide a wavelength memory section or region for storing, after a wavelength range is changed, an obtained wavelength range therein, which is utilized to form a spectral image. Such a memory section or region can be distinguished from other storage section or regions which respectively store the preliminarily set wavelength range and the optimal wavelength range corresponding to each clinical doctor. Thus, such a memory section or region can prevent an occurrence of a trouble that the wavelength range obtained in the changing operation is erroneously overwritten on the wavelength range stored in one of the other storage section or regions and is erroneously stored therein.

However, in the case where the wavelength memory section or region adapted to store, after the wavelength range is changed, the wavelength range obtained to be utilized to form a spectral image is provided separately from the other storage section or regions, usually, many operators of the apparatus frequently updates the wavelength range stored and saved in the wavelength memory section or region. Thus, in a case where a new wavelength range is set by utilizing the wavelength range stored and saved therein as a reference, the reference is frequently changed. Consequently, it is extremely likely to cause a trouble in the setting of a new wavelength range.

To prevent an occurrence of such a drawback, for example, it has been considered to automatically reset data representing the wavelength range stored in the wavelength memory section or region to an initially set value at each turnoff of a power supply due to termination of use of an endoscope apparatus. However, in this case, it is necessary to turn off the power supply each time when an operator resets the data representing the wavelength range stored in the wavelength memory section or region to the initially set value during the use of the endoscope apparatus. Consequently, the efficiency in forming and displaying a spectral image is extremely reduced.

SUMMARY OF THE INVENTION

The invention is accomplished in view of the above problems. An object of the invention is to provide an endoscope apparatus enabled to set a new wavelength range without causing a trouble and without reducing the efficiency in forming and displaying a spectral image.

According to a first aspect of the invention, there is provided an endoscope apparatus comprising an endoscope comprising an image pickup device so as to form a color image signal representing an observed object, the endoscope apparatus further comprising: a storage portion that stores matrix data regarding a wavelength range in which a spectral image is constituted; a spectral image formation circuit that performs a matrix calculation on the color image signal using the matrix data stored in the storage portion and forms a spectral image of the wavelength range; a wavelength selection section that selects the wavelength range for the spectral image which is to be formed by the spectral image formation circuit, by continuously or stepwise changing the wavelength range; a wavelength memory section comprising (i) a default data memory area that stores at least one default wavelength range and (ii) a changed-wavelength-range saving area that stores at least one wavelength range to be selected by the wavelength selection section after changed from at least one of said at least one default wavelength range; and a reset section that rewrites, when receiving a reset instruction, at least one of said at least one wavelength range stored in the changed-wavelength-range saving area into one(s) of said at least one default wavelength range stored in the default data memory area.

Incidentally, the above wavelength memory section may be implemented by a single memory having both the default data memory area and the changed-wavelength-range saving area. Alternatively, the wavelength memory section may be implemented by two memories respectively having both the default data memory area and the changed-wavelength-range saving area.

According to a second aspect of the invention, there is provided an endoscope apparatus comprising an endoscope comprising an image pickup device so as to form a color image signal representing an observed object, the endoscope apparatus further comprising: a storage portion that stores matrix data regarding a set of wavelength ranges in which a spectral image is constituted; a spectral image formation circuit that performs a matrix calculation on the color image signal using the matrix data stored in the storage portion and forms a spectral image of the set of wavelength ranges; a wavelength selection section that sets a set of wavelength ranges and selects the set of wavelength ranges by changing the set of wavelength ranges; a wavelength memory section comprising (i) a default data memory area that stores at least one set of default wavelength ranges and (ii) a changed-wavelength-range saving area that stores at least one set of wavelength ranges to be selected by the wavelength selection section after changed from at least one set of said at least one set of default wavelength ranges; and a reset section that rewrites, when receiving a reset instruction, at least one set of said at least one set of wavelength ranges stored in the changed-wavelength-range saving area into one(s) of said at least one set of default wavelength ranges stored in the default data memory area.

Incidentally, preferably, the wavelength memory section further comprises an area that stores (the set of) wavelength range(s) selected by the wavelength selection section, in addition to the default data storage area and the changed-wavelength-range saving area.

BRIEF DESCRIPTION OF THE DRAWINGS

FIG. 6 is a diagram illustrating a wavelength changing state operated by a wavelength changing switch of the endoscope apparatus shown in FIG. 1; and FIG. 7 is a diagram illustrating a wavelength set selected in a monochromatic mode in the endoscope apparatus shown in FIG. 1.

DETAILED DESCRIPTION OF THE INVENTION

Figure 1:
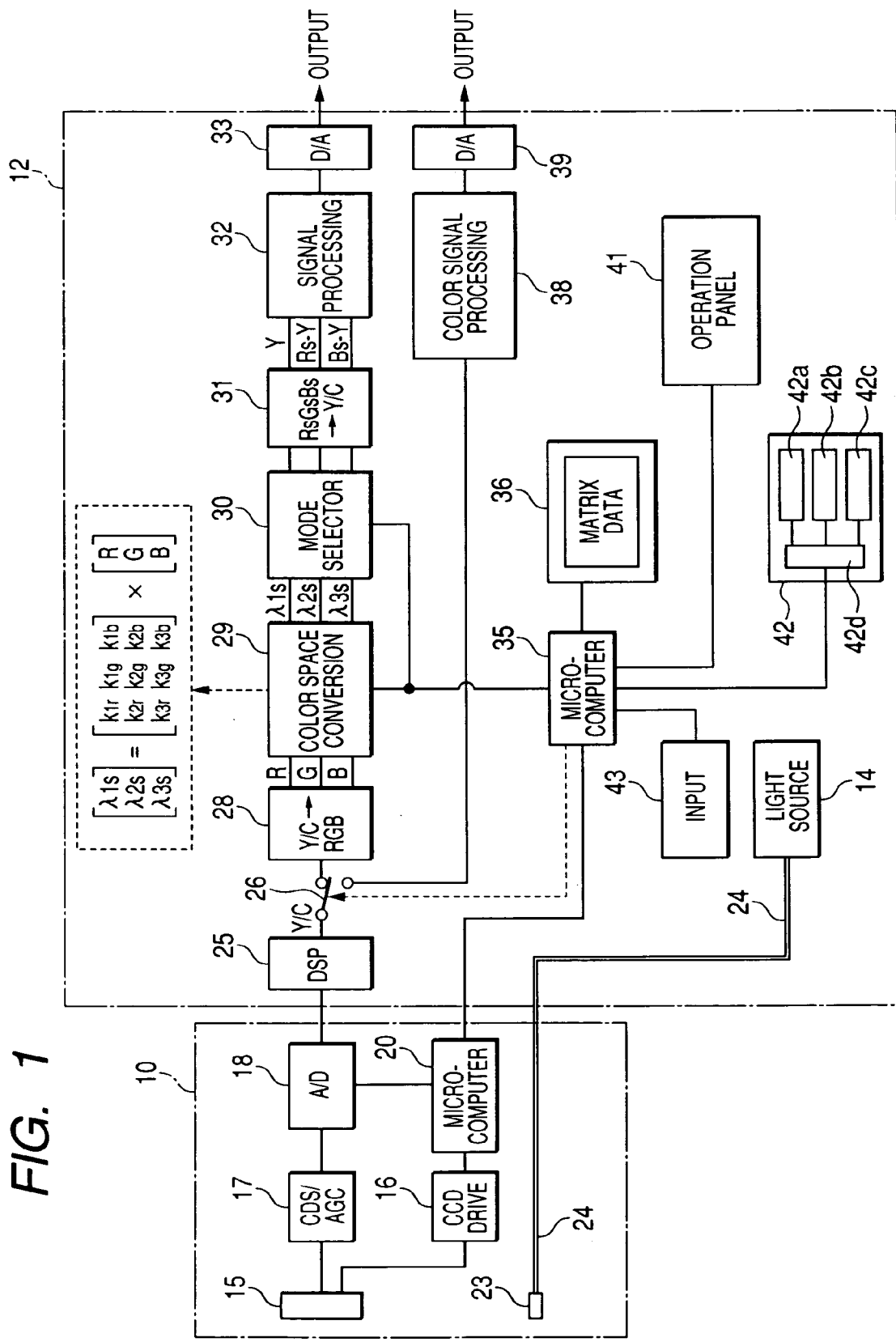
FIG. 1 is a block diagram illustrating the configuration of an endoscope apparatus according to an embodiment of the invention.

Hereinafter, an embodiment of the invention is described in detail with reference to the accompanying drawings. FIG. 1 illustrates the basic configuration of an electronic endoscope apparatus according to an embodiment of the invention. As shown in this figure, this electronic endoscope apparatus includes a scope 10, which is an endoscope body portion, and a processor unit 12 to which the scope 10 is detachably connected. A light source 12 adapted to emit white light is disposed in the processor unit 12. An illuminating window 23 is provided at an end of the scope 10. An end of the light guide 24, the other end of which is connected to the light source 14, faces the illuminating window 23. Incidentally, the light source 14 may be disposed in a light source unit separated from the processor unit 12.

A CCD 15, which is a solid-state image pickup device, is provided at an end portion of the scope 10. For example, a complementary color type CCD, which has Mg (magenta), Ye (yellow), Cy (cyan) and G (green) color filters provided on an imaging surface, or a primary-color type CCD having RGB color filters provided on an imaging surface thereof is used as the CCD 15.

A CCD drive circuit 16 adapted to form a driving pulse according to a synchronization signal is connected to the CCD 15. Also, a CDS/AGC (correlation double sampling/automatic gain control) circuit 17 is connected to the CCD 15. An A/D converter 18 is connected to the CDS/AGC circuit 17 and is adapted to digitalize an analog output of the CDS/AGC circuit 17. Also, a microcomputer 20 is disposed in the scope 10 and is adapted to control various circuits provided therein and to control communication between the scope 10 and the processor unit 12.

Meanwhile, a DSP (digital signal processor) 25 adapted to perform various kinds of image processing on a digitalized signal is provided in the processor unit 12. The DSP 25 generates and outputs a Y/C signal, which includes a luminance (Y) signal and a color-difference (C(R-Y, B-Y)) signal, from an output signal of the CCD 15. The apparatus according to the present embodiment selectively forms and displays one of a normal image and a spectral image (the both of which are moving images or still images). A changeover switch 26 adapted to switch between the formation of a normal image and that of a spectral image is connected to the DSP 25. A first color conversion circuit 28 is connected to one of output terminals of the changeover switch 26. The first color conversion circuit 28 converts a Y/C (luminance/color-difference) signal outputted from the DSP 25 into three RGB color image signals. Incidentally, the DSP 25 may be disposed in the scope 10.

A color space conversion circuit 29 adapted to perform a matrix calculation for forming a spectral image and to output image signals representing a spectral image in selected wavelength ranges $\lambda_1$, $\lambda_2$, and $\lambda_3$, a mode selector 30 adapted to select one of a monochromatic mode, in which a spectral image in a narrow wavelength band is formed, and a three-color mode in which a spectral image including components in three wavelength ranges, a second color conversion circuit 31 adapted to input image signals $\lambda_{1s}$, $\lambda_{2s}$, and $\lambda_{3s}$ in one wavelength range or three wavelength ranges as $R_s$, $G_s$, and $B_s$ signals to perform processing corresponding to RGB signals and also adapted to convert the $R_s$, $G_s$, and $B_s$ signals into Y/C signals, a signal processing circuit 32 adapted to perform other various kinds of signal processing, such as mirror image processing, mask generation, and character generation, and a D/A converter 33 are series-connected in this order to the first color conversion circuit 28 as a subsequent stage. Incidentally, a two-color mode may be set in the apparatus, instead of the three-color mode to be selected by the mode selector 30.

Also, a microcomputer 35 having the functions of performing communication between the scope 10 and the processor unit 12, controlling each of the circuits provided in the processing unit 12, and inputting matrix (or coefficient) data, which is used to form a spectral image, to the color space conversion circuit 29 is provided in the processor unit 12. Matrix data used to form a spectral image according to RGB signals is stored in the form of a table in the memory 36. Table 1 shows an example of matrix data according to the present embodiment.

TABLE 1

| Parameters | $k_{pr}$ | $k_{pg}$ | $k_{pb}$ |
|---|---|---|---|
| P1 | 0.000083 | −0.00188 | 0.003592 |
| . | . | . | . |
| . | . | . | . |
| . | . | . | . |
| P18 | −0.00115 | 0.000569 | 0.003325 |
| P19 | −0.00118 | 0.001149 | 0.002771 |
| P20 | −0.00118 | 0.001731 | 0.0022 |
| P21 | −0.00119 | 0.002346 | 0.0016 |
| P22 | −0.00119 | 0.0298 | 0.000983 |
| P23 | −0.00119 | 0.003633 | 0.000352 |
| . | . | . | . |
| . | . | . | . |
| . | . | . | . |
| P43 | 0.003236 | 0.001377 | −0.00159 |
| P44 | 0.003656 | 0.000671 | −0.00126 |
| P45 | 0.004022 | 0.000068 | −0.00097 |
| P46 | 0.004342 | −0.00046 | −0.00073 |
| P47 | 0.00459 | −0.00088 | −0.00051 |
| P48 | 0.004779 | −0.00121 | −0.00034 |
| P49 | 0.004922 | −0.00148 | −0.00018 |
| P50 | 0.005048 | −0.00172 | −0.000036 |
| P51 | 0.005152 | −0.00192 | 0.000088 |
| P52 | 0.005215 | −0.00207 | 0.000217 |
| . | . | . | . |
| . | . | . | . |
| . | . | . | . |
| P61 | 0.00548 | −0.00229 | 0.00453 |

The matrix data shown in Table 1 includes 61 wavelength range parameters (or coefficient sets) p1 to p61 respectively corresponding to intervals obtained by dividing a wavelength range from 400 nm to 700 nm by 5 nm. Each of these parameters p1 to p61 includes coefficients $k_{pr}$, $k_{pg}$, and $k_{pb}$ (p=1 to 61) used to perform matrix calculations.

Also, the color space conversion circuit 29 performs matrix calculations using the coefficients $k_{pr}$, $k_{pg}$, and $k_{pb}$ and RGB signals outputted from the first color conversion circuit 28, as shown by the following expression. Thus, spectral image signals $\lambda_{1s}$, $\lambda_{2s}$, and $\lambda_{3s}$ are formed.

$$\begin{bmatrix} \lambda_1 \\ \lambda_2 \\ \lambda_3 \end{bmatrix} = \begin{bmatrix} k_{1r} & k_{1g} & k_{1b} \\ k_{2r} & k_{2g} & k_{2b} \\ k_{3r} & k_{3g} & k_{3b} \end{bmatrix} \times \begin{bmatrix} R \\ G \\ B \end{bmatrix} \quad \text{[Equation 1]}$$

That is, in a case where, for example, 500 nm, 620 nm, and 650 nm are selected as the central wavelengths of the wavelength ranges $\lambda_1$, $\lambda_2$, and $\lambda_3$, respectively, the matrix calculations are performed by using the coefficients (−0.00119, 0.002346, 0.0016) of the parameter p21 corresponding to the central wavelength 500 nm, the coefficients (0.004022, 0.000068, −0.00097) of the parameter p45 corresponding to the central wavelength 620 nm, and the coefficients (0.005152, −0.00192, 0.000088) of the parameter p51 corresponding to the central wavelength 650 nm, as coefficients ($k_{pr}$, $k_{pg}$, $k_{pb}$), among the sixty-one parameters shown in Table 1. Incidentally, such parameters are read from the memory 36 according to the combinations of wavelengths stored in a wavelength set memory 42, which will be described later.

Also, a color signal processing circuit 38 adapted to form a normal color image, instead of a spectral image, is connected to the other output terminal of the changeover switch 26. Additionally, a D/A converter 39 is connected to the color signal processing circuit 38.

Figure 2:
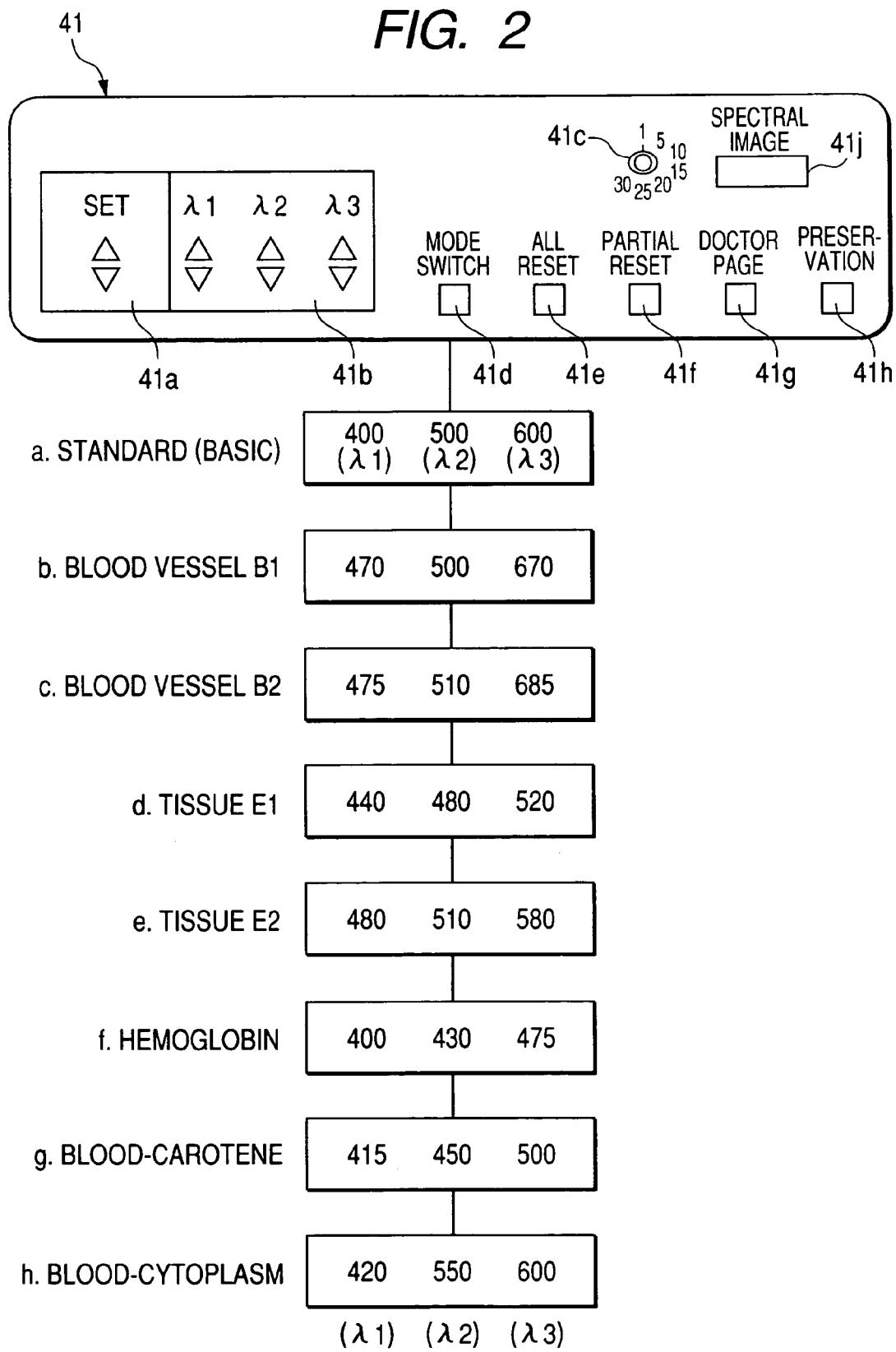
FIG. 2 is a diagram illustrating the configuration of an operation panel of a processor unit of the endoscope apparatus shown in FIG. 1 and also illustrating an example of a wavelength set.

An input portion 43 including the operation panel 41, the wavelength set memory 42, and a keyboard is connected to the microcomputer 35 in addition to the memory 36. FIG. 2 illustrates the operation panel 41 in detail. The operation panel 41 is provided with, for example, a set selection switch 41a used to select one of wavelength sets a to h, a wavelength selection switch 41b used to select one of the central wavelengths of the wavelength ranges $\lambda_1$, $\lambda_2$, and $\lambda_3$, a changing-range setting switch 41c used to set a range in which the central wavelength can be changed by the wavelength selection switch 41b, a mode change switch 41d adapted to switch between the monochromatic mode, in which a single wavelength is selected, and the three-color mode, an all-reset switch 41e used to reset each of all the wavelength sets a to h to a wavelength set represented by a default value (to be described later), a partial reset switch 41f used to reset one of the wavelength sets a to h to the wavelength set represented by the default value, a doctor page switch 41g used to write the wavelength sets a to h, which are generated corresponding to each of users, such as clinical doctors, of the apparatus, to the wavelength set memory 42 and also used to read the wavelength set therefrom, a saving switch 41h used to store and save the wavelength set in the wavelength set memory 42, and a spectral image formation switch 41j used to instruct the formation of a spectral image. These switches are schematically shown in this figure.

Hereinafter, an operation of the electronic endoscope having the above configuration according to the present embodiment is described. First, the formation of a normal image and a spectral image is described below. As shown in FIG. 1, in the scope 10, the CCD 15 driven by the CCD drive circuit 16 performs the imaging of an observed object and outputs an imaging signal. This imaging signal is amplified by undergoing correlation double sampling/automatic gain control operations at the CDS/AGC circuit 17. Subsequently, the signal undergoes A/D-conversion at the A/D converter 18. The converted signal is inputted as a digital signal to the DSP 25 of the processor unit 12.

At the DSP 25, gamma processing is performed on an output signal of the scope 10. Also, color conversion is performed on signals obtained through the Mg, Ye, Cy, and G color filters, so that Y/C signals including both a luminance (Y) signal and a color-difference (R-Y, B-Y) signal are formed. An output signal of the DSP 25 is usually supplied by the changeover switch 26 to the color signal processing circuit 38. Then, the signal undergoes predetermined kinds of processing, such as the mirror image processing, the mask generation, and the character generation, at the circuit 38. Subsequently, the signal is converted by the D/A converter 39 into analog signals. Then, the analog signal is supplied to the monitor 34 shown in FIG. 3. Consequently, a normal color image of the object is displayed in the monitor 34.

When the spectral image formation switch 41j of the operation panel 41 shown in FIG. 2 is pushed, the changeover switch 26 is changed into a state in which the Y/C signal outputted from the DSP 25 is supplied to the first color conversion circuit 28. The Y/C signals are converted by the circuit 28 into RGB signals. The RGB signals are supplied to the color space conversion circuit 29. Then, the matrix calculation represented by the equation 1 is performed using the RGB signals and the matrix data to form a spectral image. That is, in the formation of the spectral image, the three wavelength ranges $\lambda_1$, $\lambda_2$, and $\lambda_3$ are set by operating the operation panel 41 (to be described later). The microcomputer 35 reads the matrix data respectively corresponding to the three selected wavelength ranges from the memory 36. The read matrix data is inputted to the color space conversion circuit 29.

For example, in a case where the wavelengths 500 nm, 620 nm, and 650 nm are selected as the central wavelengths of the three wavelength ranges $\lambda_1$, $\lambda_2$, and $\lambda_3$, the spectral image signals $\lambda_{1s}$, $\lambda_{2s}$, and $\lambda_{3s}$ are formed by performing the matrix calculation according to the following equation 2 using the coefficients of the parameters p21, p45, and p51 shown in Table 1, respectively correspond to these central wavelengths and also using the RGB signals.

$$\begin{bmatrix} \lambda_{1s} \\ \lambda_{2s} \\ \lambda_{3s} \end{bmatrix} = \begin{bmatrix} -0.00119 & 0.002346 & 0.0016 \\ 0.004022 & 0.000068 & -0.00097 \\ 0.005152 & -0.00192 & 0.000088 \end{bmatrix} \times \begin{bmatrix} R \\ G \\ B \end{bmatrix} \quad \text{[Equation 2]}$$

In the case where the three-color mode is selected by the mode selector 30, the spectral image signals $\lambda_{1s}$, $\lambda_{2s}$, and $\lambda_{3s}$ are inputted to the second color conversion circuit 31 as three-color ($R_s$, $G_s$, $B_s$) image signals. Alternatively, in the monochromatic mode is selected by the mode selector 30, one of the spectral image signals $\lambda_{1s}$, $\lambda_{2s}$, and $\lambda_{3s}$ is inputted to the second color conversion circuit 31 as a three-color ($R_s$, $G_s$, $B_s$) image signal. At the second color conversion circuit 31, the three-color ($R_s$, $G_s$, $B_s$) image signal is converted into the Y/C signal (Y, $R_s$-Y, $B_s$-Y) This Y/C signal is inputted to the monitor 34 through the signal processing circuit 32 and the D/A converter 33.

Figure 4:
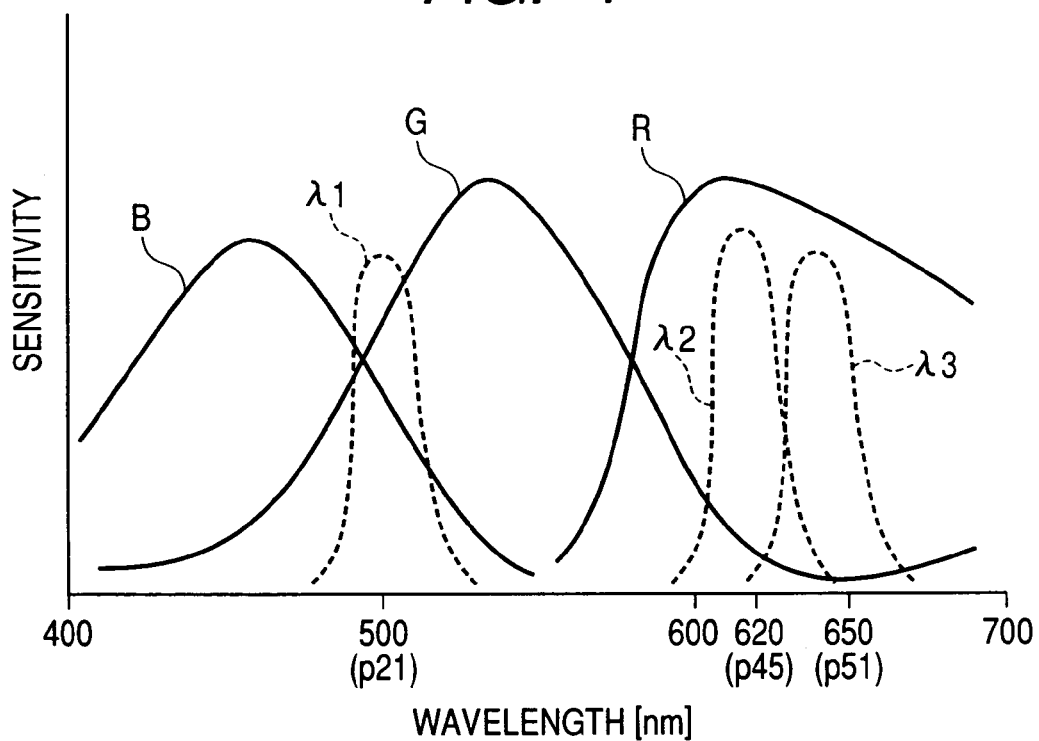
FIG. 4 is a graph illustrating an example of a wavelength range of a spectral image together with a spectral sensitivity of a primary-color CCD.
Figure 5:
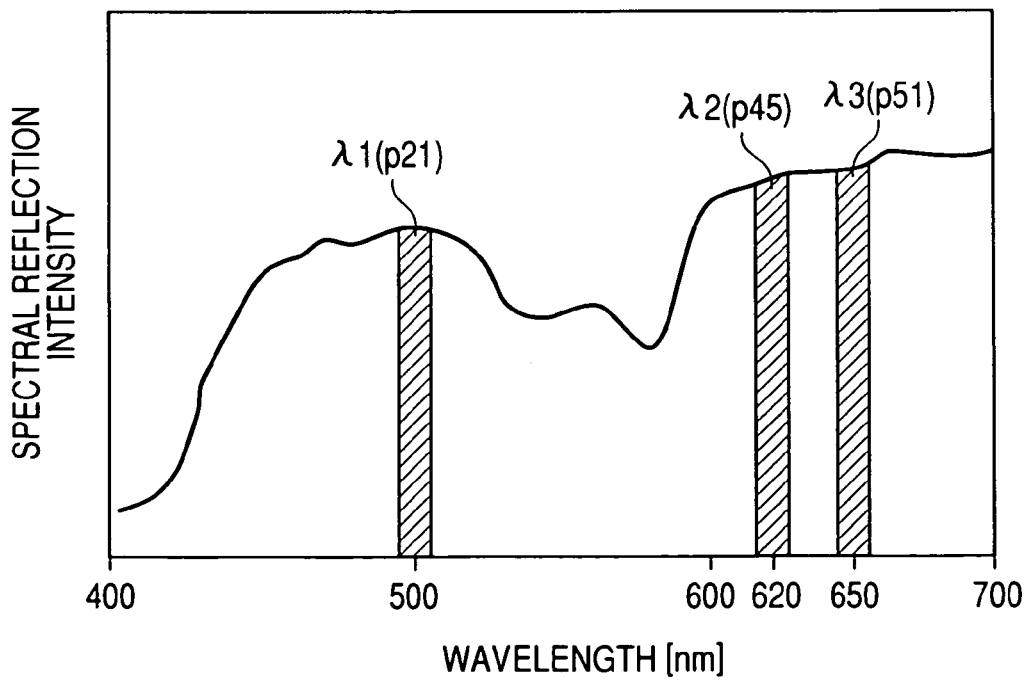
FIG. 5 is a graph illustrating an example of a wavelength range of a spectral image together with reflection spectra of a living organism.

Thus, the spectral image displayed in the monitor 34 includes color components in the wavelength ranges, as shown in FIGS. 4 and 5. That is, FIG. 4 is a conceptual graph showing curves representing spectra in the tree wavelength ranges $\lambda_1$, $\lambda_2$, and $\lambda_3$, to be superimposed on curves representing spectral sensitivity characteristics R, G, and B of the primary color type color filter. FIG. 5 is a conceptual graph showing curves representing spectra in the tree wavelength ranges $\lambda_1$, $\lambda_2$, and $\lambda_3$ to be superimposed on curves representing reflection spectra of a living organism. The spectral image signals $\lambda_{1s}$, $\lambda_{2s}$, and $\lambda_{3s}$ illustrated by using the parameters P21, p45, and p51 are color signals in the wavelength ranges each of which has a central wavelength at an associated one of 500 nm, 620 nm, and 650 nm and ranges from (the associated central wavelength–about 10 nm) to (the associated central wavelength+about 10 nm). Thus, spectral images (including a moving image and a still image) formed from the combinations of colors in the three wavelength ranges are displayed.

Incidentally, in a case where the changeover switch 26 is in a state in which the Y/C signal outputted from the DSP 25 is supplied to the first color space conversion circuit 28, and where the spectral image is formed and displayed, when the spectral image formation switch 41*j* of the operation panel 41 shown in FIG. 2 is pushed, the changeover switch 26 is put back to a state in which the Y/C signal is supplied to the color signal processing circuit 38, a normal color image, which is a moving image or a still image, is displayed.

Next, the selection of the wavelength ranges $\lambda_1$, $\lambda_2$, and $\lambda_3$ is described below. According to the present embodiment, as shown in FIG. 2, for example, the following 8 wavelength sets are stored in the first area 42*a* of the wavelength set memory 42 as the wavelength set of the central wavelengths respectively corresponding to the wavelength ranges $\lambda_1$, $\lambda_2$, and $\lambda_3$. That is, a standard set a of the central wavelengths of 400, 500, and 600 (nm (similarly, the unit of the central wavelength is nm in the remaining sets)), a blood vessel B1 set b of the central wavelengths of 470, 500, and 670 for drawing a blood vessel, similarly, a blood vessel B2 set c of the central wavelengths of 475, 510, and 685 for drawing a blood vessel, a tissue E1 set d of the central wavelengths of 440, 480, and 520 for drawing a specific tissue, similarly, a tissue E2 set e of the central wavelengths of 480, 510, and 580 for drawing a specific tissue, a hemoglobin set f of the central wavelengths of 400, 430, and 475 for drawing the difference between oxyhemoglobin and deoxyhemoglobin, a blood-carotene set g of the central wavelengths of 415, 450, and 500 for drawing the difference between blood and carotene, and a blood-cytoplasm set h of the central wavelengths of 420, 550, and 600 for drawing the difference between blood and cytoplasm.

At the factory shipment of the electronic endoscope, the default wavelength sets stored in the first area 42*a* is also stored in a second area 42*b* of the wavelength set memory 42. Thereafter, when the apparatus is first started up by turning on the power supply, the microcomputer 35 selects the default wavelength sets stored in the second area 42*b*. Subsequently, when the spectral image formation switch 41*j* shown in FIG. 2 is pushed, the standard set a of the selected wavelength sets is displayed on a wavelength information display area 34*s* of the monitor 34. At that time, in a case where the three-color mode has been selected by pushing the mode switch 41*d*, the parameters respectively corresponding to the central wavelengths of the wavelength ranges $\lambda_1$, $\lambda_2$, and $\lambda_3$ of the standard set a, that is, 400 nm, 500 nm, and 600 nm are read from the memory 36. The read parameters are inputted to the color space conversion circuit 29. Then, the color space conversion circuit 29 performs the matrix calculation using the inputted parameters thereby to form the spectral image signals $\lambda_{1s}$, $\lambda_{2s}$, and $\lambda_{3s}$. Subsequently, the spectral image represented by the spectral image signals $\lambda_{1s}$, $\lambda_{2s}$, and $\lambda_{3s}$ is displayed in the monitor 34 shown in FIG. 3A.

The operator, such as a clinical doctor, of the apparatus can optionally select one of the other wavelength sets b to h of the default wavelength sets by operating the set selection switch 41*a* of the operation panel 41 shown in FIG. 2. The microcomputer 35 causes the monitor 34 shown in FIG. 3 to display the selected wavelength set on the wavelength information display area 34*s*. Also, in this case, the parameters respectively corresponding to the central wavelengths of the wavelength ranges $\lambda_1$, $\lambda_2$, and $\lambda_3$ of the selected wavelength set are read from the memory 36 by the microcomputer 35. The read parameters are inputted to the color space conversion circuit 29. Then, the color space conversion circuit 29 performs the matrix calculation using the inputted parameters thereby to form the spectral image signals $\lambda_{1s}$, $\lambda_{2s}$, and $\lambda_{3s}$. Subsequently, the spectral image represented by the spectral image signals $\lambda_{1s}$, $\lambda_{2s}$, and $\lambda_{3s}$ is displayed in the monitor 34 shown in FIG. 3A

Incidentally, as shown in FIG. 2, the set selection switch 41*a* includes an ascending switch, which has an upward triangular operation part, and a descending switch that has a downward triangular operation part. Each time when the former part is pushed one time, the wavelength set is sequentially selected like a→h→g . . . →a. Conversely, each time when the latter part is pushed one time, the wavelength set is sequentially selected like a→b→c . . . →a.

Also, when one of the wavelength sets a to h is selected, the operator can change the wavelength ranges $\lambda_1$, $\lambda_2$, and $\lambda_3$ of the selected wavelength set to optional values by operating the wavelength selection switch 41b. At the change of the wavelength ranges, a wavelength changing range can be changed by the changing-range setting switch 41b. That is, the changing range can be continuously or stepwise changed by turning the knob of the changing-range setting switch 41c so that a changing pitch is set to be 1 nm to achieve a substantially continuous change, and that the changing pitch is set to be 5 nm, 10 nm, or 2 nm to achieve a stepwise change. Incidentally, for example, in the case of changing the range at a pitch of 1 nm, 301 wavelength ranges can be set within a range from 400 nm to 700 nm. Then, matrix data P'1 to p'301 respectively corresponding to the 301 wavelength ranges are generated.

FIG. 6 illustrates such selection of the wavelength range. When the changing pitch is set to be 5 nm, the wavelength range is changed like 400→405→410, similarly to the case of $\lambda_1$. When the changing pitch is set to be 20 nm, the wavelength range is changed like 600→620→640, similarly to the case of $\lambda_3$. These values are displayed on the wavelength information display area 34s of the monitor 34.

Figure 3A:
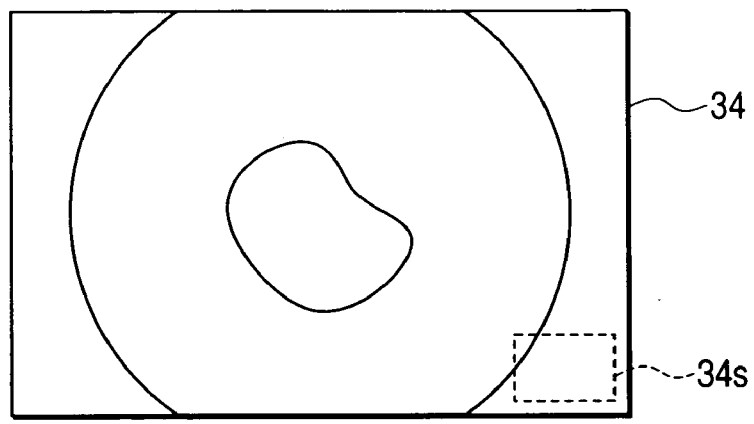
FIGS. 3A to 3C are diagrams illustrating a wavelength information display area of the screen of a monitor of the endoscope apparatus shown in FIG. 1 and an example of display of wavelength information.
Figure 3B:
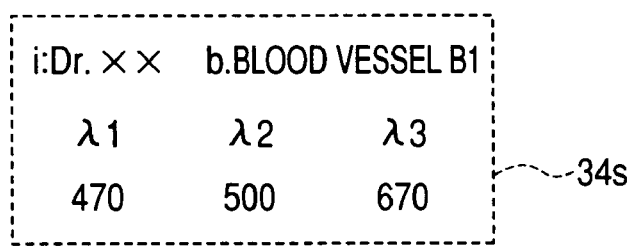
Figure 3C:
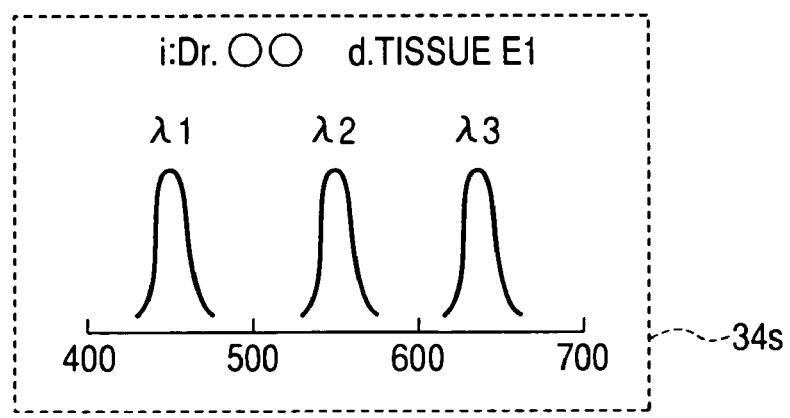

FIGS. 3A to 3C show a display state of the wavelength information display area 34s in detail. According to the present embodiment, as viewed in FIG. 3A, wavelength information is displayed on the wavelength information display area 34s, which is set at a rightwardly downward part of the monitor 34, by character generation performed at the signal processing circuit 32. That is, as illustrated in FIG. 3B, the selected wavelength value (represented in nm) is shown under characters, such as $\lambda_1$, $\lambda_2$, and $\lambda_3$ on the wavelength information display area 34s. Alternatively, as shown in FIG. 3C, abscissas represent wavelengths, while ordinates represent sensitivity. The selected wavelength range may be visually displayed by using a movable graph (corresponding to FIG. 4).

Incidentally, an operation of changing the values of the central wavelengths of the wavelength ranges $\lambda_1$, $\lambda_2$, and $\lambda_3$ corresponding to the wavelength set to optional values is performed by utilizing the work area 42d of the wavelength set memory 42 shown in FIG. 2.

The mode switch 41d shown in FIG. 2 is used to switch between the monochromatic mode and the three-color mode. In a case where the mode switch 41d is pushed in the three-color mode, an operation mode is changed to the monochromatic mode. Then, the microcomputer 35 changes all the central wavelengths of the wavelength ranges $\lambda_1$, $\lambda_2$, and $\lambda_3$ to the same value of 470. As shown in FIG. 7, the common wavelength range is indicated in the monitor 34. Incidentally, an optional value can be selected by the wavelength selection switch 41b as the central wavelength of the common wavelength range.

Incidentally, a part of the functions of the switches of the operation panel 41 may be replaced with the functions of keys of a keyboard. Alternatively, all the functions of the switches of the operation panel 41 may be replaced with the functions of keys of a keyboard.

As described above, in a case where the wavelength ranges $\lambda_1$, $\lambda_2$, and $\lambda_3$ to corresponding to some of the wavelength sets a to h are changed, when the saving switch 41h provided on the operation panel 41 shown in FIG. 2 is pushed, new wavelength sets a to h including the wavelength ranges, the wavelength ranges corresponding to which are changed, are overwritten and saved in the second area 42b of the wavelength memory 42 by the microcomputer 35. The saving of the new wavelength sets a to h is convenient for the case of immediately forming and displaying a spectral image utilizing the new wavelength sets a to h.

Also, the new wavelength sets a to h are newly stored and saved in a third area 42c of the wavelength set memory by the microcomputer 35 by, for example, simultaneously pushing the saving switch 41h and the doctor page switch 41g provided on the operation panel 41 shown in FIG. 2. At that time, a guidance indication suggesting the input of a name of the operator saving the new wavelength sets is displayed in the monitor 34. Then, the name, for example, "Dr. XX" is inputted by utilizing the input portion 43, such as the keyboard shown in FIG. 1. The microcomputer 35 causes the memory 42 to store the new wavelength sets a to h by associating the new wavelength sets a to h with the inputted name. According to the present embodiment, the wavelength sets a to h can be stored as an example to a maximum of ten wavelength sets by being associated with the name of the operator of the apparatus.

The wavelength sets a to h stored in the third area 42c of the memory 42 can be read from the third area 42c and used by pushing the doctor page switch 41g provided on the panel 41. That is, each time when the doctor page switch 41g is pushed once, the wavelength sets are sequentially selected like the first wavelength set a to h, the second wavelength set a to h, the third wavelength set a to h, . . . . Then, the selected wavelength set is read from the third area 42c and is stored in the second area 42b serving as a changed wavelength saving area. Subsequently, the parameters for the wavelength regions $\lambda_1$, $\lambda_2$, and $\lambda_3$ corresponding to the stored wavelength set are read from the memory 36 by the microcomputer 35. The formation of a spectral image is performed in a manner similar to the previously described manner.

Incidentally, as illustrated in FIGS. 3B and 3C, the indication of a creator and a set name, such as "Dr. XX b. Blood Vessel B1", is displayed, together with the indication of "i" representing the formation of a spectral image, on the wavelength information display area 34s of the monitor 34. Consequently, the wavelength set, according to which a spectral image is formed and displayed, can be checked.

Wavelength ranges $\lambda_1$, $\lambda_2$, and $\lambda_3$ optimal in forming and displaying a clinically easily observable spectral image often vary with operators, such as a clinical doctor, of the apparatus. However, in a case where one wavelength set corresponding to each operator of the apparatus is preliminarily generated, saved and adapted to be able to be used by being read, a most easily observable spectral image for each operator can quickly and easily be formed.

When the indication "Dr. XX b. Blood Vessel B1" is displayed corresponding to the wavelength set, it is convenient for knowing the history of the wavelength set to use different colors to display the indication. For example, in a case where the used wavelength set is the default wavelength set, the indication is displayed with white. In a case where the used wavelength set is obtained by changing the default wavelength set, the indication is displayed with green.

Similarly to the case of changing the default wavelength set a to h read from the first area 42a as described above, the wavelength ranges $\lambda_1$, $\lambda_2$, and $\lambda_3$ corresponding to part or all of the wavelength sets a to h read from the third area 42c of the wavelength set memory 42 can be changed. The wavelength sets a to h changed in this way are overwritten and saved in the third area 42c of the wavelength set memory 42 shown in FIG. 1 by pushing the saving switch 41h provided on the operation panel 41. That is, in a case where the wavelength set is a first group of wavelength sets generated by the "Dr. XX", the changed wavelength sets a to h are saved as a new first group of wavelength sets.

Also, the wavelength sets a to h changed in the aforementioned manner can be stored and saved in the third area 42c of the wavelength set memory 42 shown in FIG. 1 as a new group of wavelength sets by simultaneously pushing the saving switch 41*h* and the doctor page switch 41*g* provided on the operation panel 41. At that time, the guidance indication suggesting the input of the name of the operator saving the new wavelength sets is displayed in the monitor 34. Then, the name, for example, "Dr. XX" is inputted by utilizing the input portion 43, such as the keyboard shown in FIG. 1. The microcomputer 35 causes the memory 42 to store the new wavelength sets a to h in the third area 42*c* by associating the new wavelength sets a to h with the inputted name. Consequently, for example, a clinically inexperienced operator of the apparatus can easily generate a wavelength set, which is fitted to this operator, by partly borrowing the wavelength sets a to h generated by a clinically experienced operator of the apparatus.

Incidentally, instead of simultaneously pushing the saving switch 41*h* and the doctor page switch 41*g* as described above, the following operation may be performed. That is, only the saving switch 41*h* is pushed. Simultaneously, the indication "Do you overwrite?" is displayed in the monitor 34. In a case where an affirmative indication is inputted in response to the indication, the wavelength sets are overwritten on the read group of wavelength sets. Conversely, in a case where a negative indication is inputted in response to the indication, the wavelength sets may be newly stored and saved as a group of wavelength sets, which differs from the read group of wavelength sets.

Next, the reset of the wavelength sets stored in the second area 42*b* of the wavelength set memory 42 is described below. The default wavelength set stored in the second area 42*b* is changed, as described above. A spectral image is formed and displayed according to the changed wavelength set. Subsequently, the all reset switch 41*e* provided on the operation panel 41 is pushed. Then, the microcomputer 35 reads the default wavelength set stored in the first area 42*a* of the wavelength set memory 42, and causes the memory 42 to store the read default wavelength set in the second area 42*b*.

Preferably, this reset operation is always performed, for example, after a spectral image is formed and displayed. Consequently, the generation of a new wavelength set based on the wavelength set stored in the second area 42*b* is always performed according to the default wavelength set, regardless of who is the operator of the apparatus. This prevents a trouble from occurring in the formation of a new wavelength set due to the presence of a plurality of reference wavelength sets.

When the partial reset switch 41*f* provided on the operation panel 41 shown in FIG. 2 is pushed after the default wavelength set stored in the second area 42*b* is changed as described above and a spectral image is formed and display according to the changed wavelength set, the microcomputer 35 causes the memory 42 to store the wavelength set (one of the wavelength sets a to h) of the corresponding group in the second area 42*b*, among the groups of the wavelength sets stored in the first area 42*a*, instead of one of the wavelength sets a to h, which has been used to form the spectral image. Consequently, in a case where an operator is confused about which set of the wavelength ranges $\lambda_1$, $\lambda_2$, and $\lambda_3$ is the best, while one of the wavelength sets a to h is variously changed, the changed default wavelength set is reset to the reference default wavelength set. This can resolve the confusion.

Next, the reset of the wavelength set stored in the third area 42*c* of the wavelength set memory 42 is described below. The wavelength set corresponding to each operator, which is stored in the third area 42*c*, is changed, as described above. A spectral image is formed and displayed according to the changed wavelength set. Subsequently, when the all reset switch 41*e* provided on the operation panel 41 shown in FIG. 2 is pushed, the microcomputer 35 reads the default wavelength set stored in the first area 42*a* of the wavelength set memory 42 and causes the memory 42 to store the read default wavelength set in the third area 42*c*.

Alternatively, the wavelength set corresponding to each operator, which is stored in the third area 42*c*, is changed, as described above. A spectral image is formed and displayed according to the changed wavelength set. Subsequently, when the partial reset switch 41*f* provided on the operation panel 41 shown in FIG. 2 is pushed, the microcomputer 35 causes the memory 42 to store the wavelength set (one of the wavelength sets a to h) of the corresponding group in the third area 42*c*, among the groups of the wavelength sets stored in the first area 42*a*, instead of one of the wavelength sets a to h, which has been used to form the spectral image.

One of the above reset operations is performed. Consequently, in a case where an operator is confused about which set of the wavelength ranges $\lambda_1$, $\lambda_2$, and $\lambda_3$ is the best, while one or a plurality of the wavelength sets a to h are variously changed, the changed default wavelength set is reset to the reference default wavelength set. This can resolve the confusion.

Incidentally, the above embodiment is adapted so that a wavelength range from 400 nm to 700 nm is divided into 61 wavelength ranges, and that one of the 61 wavelength ranges can be selected. However, a spectral image, which is close to an image conventionally obtained by irradiating infrared light rays, can be obtained without a visible light cutoff filter by selecting wavelength sets in wavelength ranges including an infrared range or only in infrared ranges as the wavelength ranges $\lambda_1$, $\lambda_2$, and $\lambda_3$. Hitherto, fluorescence emitted from a cancer tissue, onto which exciting light is irradiated, has been imaged by a related endoscope. Wavelengths adjusted to the wavelengths of fluorescence are selected as those of the wavelength set in the wavelength ranges $\lambda_1$, $\lambda_2$, and $\lambda_3$. Thus, a spectral image of a part emitting fluorescence can be formed. In this case, an advantage in eliminating the necessity of an exciting light cutoff filter is obtained.

Hitherto, pigments, for example indigo and Pyoktanin® have been scattered onto an observed object. Tissues colored with the pigments have been imaged by a related endoscope. Wavelength ranges enabled to draw the tissues colored with scattered pigments are selected as those of the wavelength set in the wavelength ranges $\lambda_1$, $\lambda_2$, and $\lambda_3$. Thus, a spectral image substantially equivalent to an image obtained in the case of scattering pigments can be obtained without scattering pigments.

The endoscope apparatus according to the invention includes the wavelength memory section having the default data memory area adapted to store the default value representing the wavelength range selected by the wavelength selection section, and also having the changed-wavelength saving area adapted to store the wavelength range selected by the wavelength selection section after changed from the wavelength range represented by the default value, and also includes the reset section adapted to rewrite, when receiving the reset instruction, at least a part of the wavelength range stored in the changed-wavelength saving area into the default value stored in the default data memory area. Thus, the wavelength range stored in the changed-wavelength-range can be reset to the wavelength range, which is represented by the default value, by operating the reset section.

In a case where the wavelength range stored and saved in the wavelength memory section is utilized as a reference, and where a new wavelength range is set according to this reference, the reference can be reset to a specific wavelength range by operating such a reset operation. Thus, the new wavelength range can be set without causing a trouble.

Also, the above reset operation can be performed at any point in time. Thus, it is unnecessary to turn off the power supply to reset the apparatus. Consequently, the efficiency in forming and displaying a spectral image is not degraded by resetting the apparatus.

The entire disclosure of each and every foreign patent application from which the benefit of foreign priority has been claimed in the present application is incorporated herein by reference, as if fully set forth.

What is claimed is:

1. An endoscope apparatus comprising an endoscope comprising an image pickup device so as to form a color image signal representing an observed object, the endoscope apparatus further comprising:
    a storage portion that stores matrix data regarding a wavelength range in which a spectral image is constituted;
    a spectral image formation circuit that performs a matrix calculation on the color image signal using the matrix data stored in the storage portion so as to form a spectral image of the wavelength range;
    a wavelength selection section, included in an operational panel, that selects the wavelength range for the spectral image which is to be formed by the spectral image formation circuit, by continuously or stepwise changing the wavelength range;
    a wavelength memory section comprising (i) a default data memory area that stores at least one default wavelength range and (ii) a changed-wavelength-range saving area that stores at least one wavelength range to be selected by the wavelength selection section after changed from at least one of said at least one default wavelength range; and
    a reset section, included in said operational panel, that rewrites, when receiving a reset instruction, at least one of said at least one wavelength range stored in the changed-wavelength-range saving area into one(s) of said at least one default wavelength range stored in the default data memory area.

2. An endoscope apparatus comprising an endoscope comprising an image pickup device so as to form a color image signal representing an observed object, the endoscope apparatus further comprising:
    a storage portion that stores matrix data regarding a set of wavelength ranges in which a spectral image is constituted;
    a spectral image formation circuit that performs a matrix calculation on the color image signal using the matrix data stored in the storage portion so as to form a spectral image of the set of wavelength ranges;
    a wavelength selection section, included in an operational panel, that sets a set of wavelength ranges and selects the set of wavelength ranges by changing the set of wavelength ranges for the spectral image which is to be formed by the spectral image formation circuit, by continuously or stepwise changing the wavelength range;
    a wavelength memory section comprising (i) a default data memory area that stores at least one set of default wavelength ranges and (ii) a changed-wavelength-range saving area that stores at least one set of wavelength ranges to be selected by the wavelength selection section after changed from at least one set of said at least one set of default wavelength ranges; and
    a reset section, included in said operational panel, that rewrites, when receiving a reset instruction, at least one set of said set of wavelength ranges stored in the changed-wavelength-range saving area into one(s) of said at least one set of default wavelength ranges stored in the default data memory area.

3. The endoscope apparatus according to claim 1, wherein the wavelength memory section further comprises an area that stores the wavelength range selected by the wavelength selection section, in addition to the default data storage area and the changed-wavelength-range saving area.

4. The endoscope apparatus according to claim 2, wherein the wavelength memory section further comprises an area that stores the set of wavelength ranges selected by the wavelength selection section, in addition to the default data storage area and the changed-wavelength-range saving area.

* * * * *